(12) United States Patent
Kornfield et al.

(10) Patent No.: US 7,241,009 B2
(45) Date of Patent: Jul. 10, 2007

(54) CROSSLINKING OF SILICONES PRESENCE OF FUNCTIONALIZED SILICONES

(75) Inventors: Julia A. Kornfield, Pasadena, CA (US); Robert H. Grubbs, South Pasadena, CA (US); Shiao H. Chang, Pasadena, CA (US); Jagdish M. Jethmalani, San Diego, CA (US)

(73) Assignee: Calhoun Vision, Inc., Pasadena, CA (US)

( * ) Notice: Subject to any disclaimer, the term of this patent is extended or adjusted under 35 U.S.C. 154(b) by 363 days.

(21) Appl. No.: 10/871,686

(22) Filed: Jun. 17, 2004

(65) Prior Publication Data

US 2005/0018310 A1    Jan. 27, 2005

Related U.S. Application Data

(63) Continuation-in-part of application No. 09/991,560, filed on Nov. 21, 2001, now abandoned.

(51) Int. Cl.
*G02C 7/02*    (2006.01)
(52) U.S. Cl. ...................................................... 351/159
(58) Field of Classification Search ................ 359/642; 623/901; 528/21; 564/18; 351/159
See application file for complete search history.

(56) References Cited

U.S. PATENT DOCUMENTS

| 4,259,467 A | 3/1981 | Keogh et al. |
| 4,260,725 A | 4/1981 | Keogh et al. |
| 4,853,438 A | 8/1989 | Bernhardt et al. |
| 4,853,483 A * | 8/1989 | Bright .......................... 564/18 |
| 5,411,553 A | 5/1995 | Gerace et al. |
| 6,103,847 A * | 8/2000 | Lewis et al. ................... 528/21 |
| 6,450,642 B1 | 9/2002 | Jethmalani et al. |

* cited by examiner

*Primary Examiner*—George Manuel
(74) *Attorney, Agent, or Firm*—Fulbright & Jaworski LLP

(57) ABSTRACT

Methods and materials are disclosed for the production of optical elements, in particular intraocular lenses (IOL) that incorporate any amount (0 to 99%) of refraction and/or shape modulating compound into a substantially crosslinked first polymeric matrix. The materials produced according to the inventive methods exhibit certain rheological parameters useful in defining medical lenses. These medical lenses have the ability to change their refractive power via changing the refractive index and/or by altering the shape by stimulus induced polymerization.

Figure 1:
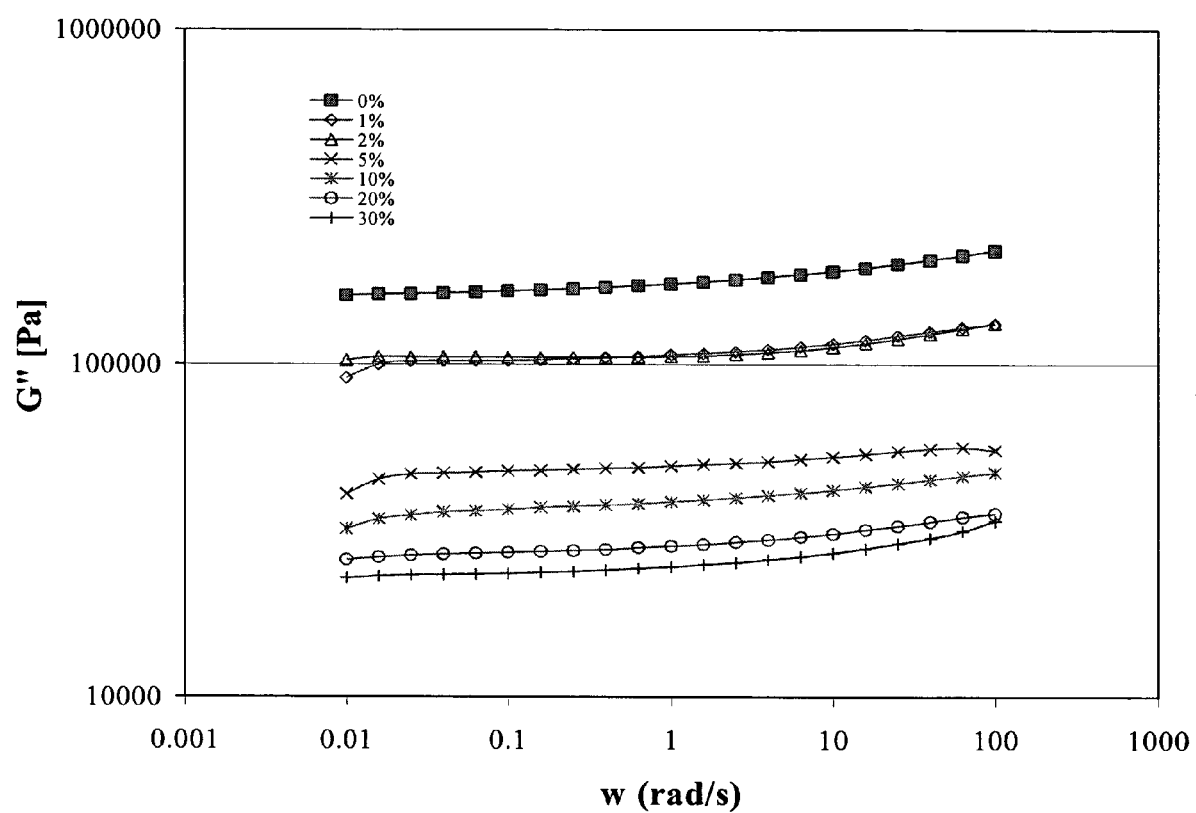

30 Claims, 2 Drawing Sheets

CROSSLINKING OF SILICONES PRESENCE OF FUNCTIONALIZED SILICONES This application is a Continuation In Part (CIP) of U.S. Regular application Ser. No. 09/991,560 filed Nov. 21, 2001, now abandoned which is hereby incorporated by reference in its entirety.

BACKGROUND

Approximately two million cataract surgery procedures are performed in the United States annually. The procedure generally involves making an incision in the anterior lens capsule to remove the cataractous crystalline lens and implanting an intraocular lens in its place. The power of the implanted lens is selected (based upon pre-operative measurements of ocular length and corneal curvature) to enable the patient to see without additional corrective measures (e.g., glasses or contact lenses). Unfortunately, due to errors in measurement, and or variable lens positioning and wound healing, about half of all patients undergoing this procedure will not enjoy optimal vision without correction after surgery. Brandser et al., *Acta Ophthalmol Scand* 75: 162-165 (1997); Oshika et al., *J cataract Refract Surg* 24:509-514 (1998). Because the power of prior art intraocular lenses generally cannot be adjusted once they have been implanted, the patient typically must choose between replacing the implanted lens with another lens of a different power or be resigned to the use of additional corrective lenses such as glasses or contact lenses. Since the benefits typically do not outweigh the risks of the former, it is almost never done.

An intraocular lens whose power may be adjusted after implantation and subsequent wound healing would be an ideal solution to post-operative refractive errors associated with cataract surgery. Moreover, such a lens would have wider applications and may be used to correct more typical conditions such as myopia, hyperopia, and astigmatism. Although surgical procedures such as LASIK which uses a laser to reshape the cornea are available, only low to moderate myopia and hyperopia may be readily treated. In contrast, an intraocular lens, that would function just like glasses or contact lenses to correct for the refractive error of the natural eye, could be implanted in the eye of any patient. Because the power of the implanted lens may be adjusted, post-operative refractive errors due to measurement irregularities and/or variable lens positioning and wound healing may be fine tuned in-situ. Accordingly, there exists an ongoing need for improved materials for such implanted lenses, e.g. materials with a range of mechanical and/or optical properties, whose refractive power can be modified via change in refractive index and/or shape after an implant is in place. More specifically, a need exists for implant materials that can be prepared to accommodate a broad range of patients whereby the implant can be suitably formulated and modified post-formation without resort to further invasive procedures.

SUMMARY

The present invention relates to materials for optical elements, particularly materials for medical lenses, methods of producing such materials, and using the same. In general, the method of the invention for fabricating an optical element comprises (a) preparing a first composite comprising a first precursor and a refraction- and/or shape-modifying composition (RSMC or RMC); (b) preparing a second composite, comprising a second precursor and a catalyst of the first and second precursors; (c) combining the first and the second composites to form a reaction mixture; (d) placing the reaction mixture into a mold; (e) forming a substantially crosslinked first polymer matrix from the reaction mixture, where the substantially crosslinked first polymer matrix having the RSMC dispersed therein, and; (f) removing the optical element from the mold. The method may be practiced using variations in temperature(s) and pressure(s) and various ratios of precursors, RSMC and catalyst. Certain embodiments of the invention may be used to prepare materials especially suitable for IOLs (implantable intraocular lenses) exhibiting a preferred useful range of viscoelastic properties, for example, shear modulus, G', or shear loss modulus G"(an indicator of crosslinking in polymer systems). When at least a portion of an IOL prepared according to the preferred methods of the invention is exposed to an appropriate stimulus, for example UV radiation, the refraction- and/or shape-modifying modulating composition (RSMC) forms a second reaction product that may be polymeric and that may further result in the formation of an interpenetrating polymer network (IPN). The formation of the second reaction product, in any form, modifies lens refractive power by changing its refractive index and/or shape (radius of curvature).

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTIONS OF THE DRAWINGS

FIG. 1 is a graphical plot showing the effect on the viscoelastic shear loss modulus, G", caused by varying the quantities of one RSMC from 0 to 30 weight % in a substantially crosslinked first polymer matrix prepared according to embodiments of the present invention.

Figure 2:
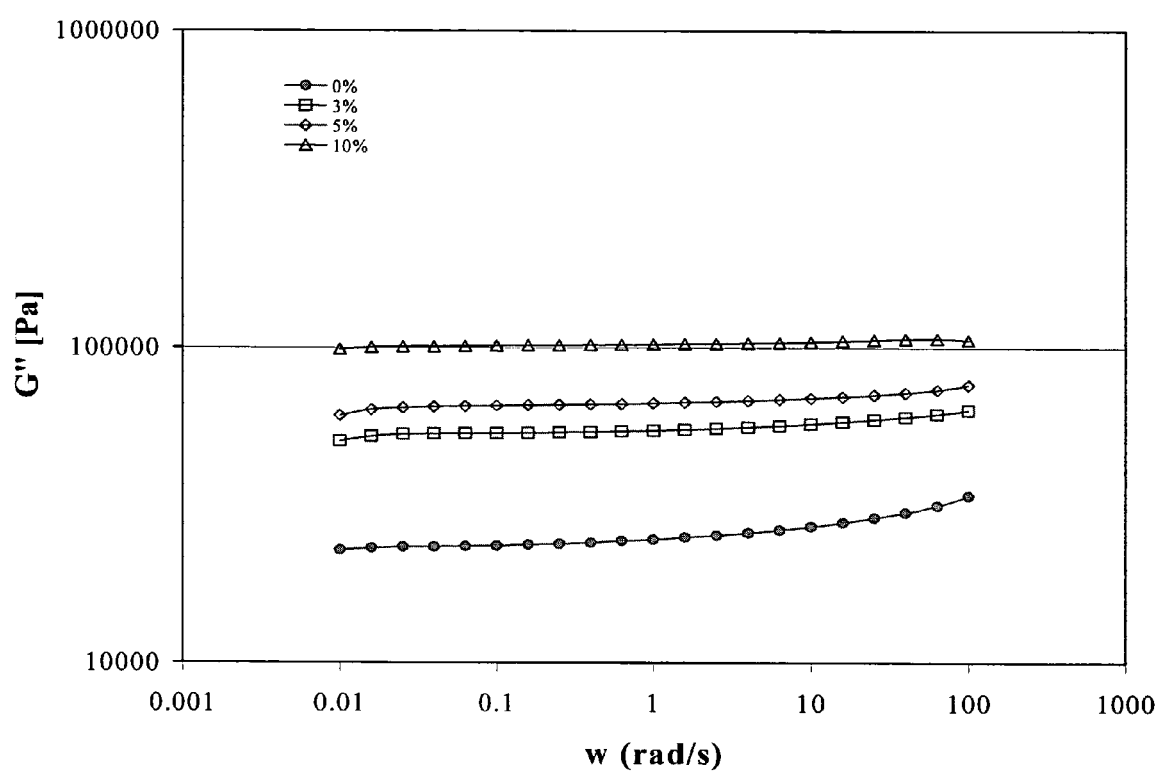

FIG. 2 is graphical plot showing the effect on the viscoelastic shear loss modulus, G", caused by varying quantities from 0 to about 10 weight % of acrosslinking agent incorporated into a substantially crosslinked first polymer matrix containing about 30% of a RSMC compound prepared according to embodiments of the invention.

DETAILED DESCRIPTION OF THE PREFERRED EMBODIMENTS

The present invention relates to methods for preparing substantially crosslinked first polymeric materials, in particular polysiloxane-based materials, that possess preferably certain values of mechanical properties, such as the elastic shear loss modulus, G", useful in optical elements (e.g., medical lenses) that are capable of post-fabrication modifications. More particularly, the present invention relates to methods for producing materials for intraocular lenses (IOLs) whose optical properties, e.g. power, may be adjusted in-situ after a lens prepared according to embodiments of the present invention is implanted in the eye. Alternatively, the optical properties may be adjusted ex-vivo as a manufacturing step to customize the lens.

The inventive methods produce materials suitable for optical elements such as IOLs and the like. The method generally comprises (a) preparing a first composite comprising a first precursor, a crosslinkg agent and a refraction-and/or shape-modifying composition (RSMC); (b) preparing a second composite comprising a second precursor and a catalyst to react the first and second precursors; (c) combining the first and second composites to form a reaction mixture; (d) placing the reaction mixture into a mold; (e) forming a substantially crosslinked first polymer matrix from the reaction mixture, where the substantially crosslinked first polymer matrix has the RSMC dispersed therein, and; (f) removing the optical element from the mold.

The substantially crosslinked first polymer matrix forms an optical element framework of a lens and is generally responsible for many of its material properties. The term "substantially crosslinked polymer matrix" as used herein refers to a synthesized material, in particular a silicone-based material, that is capable of utility in an optical element, preferably a lens, more preferably an intraocular lens that is formed by the reaction of the composite precursors. The reactive materials in the matrix need not be exhaustively reacted: that is, a highly crosslinked matrix need not be formed. But rather, the method may be utilized to prepare materials having a range of crosslinking densities so as to facilitate the formation of various embodiments of optical elements. Such variations in the material properties (for example the elastic shear loss modulus, G") of optical elements allow tailoring of lenses for a particular type of patient.

In one embodiment of the method the two or more precursors that form the substantially crosslinked first polymer matrix are reacted in the presence of the refraction and/or shape modifying modulating composition (RSMC) using a catalyst. In another embodiment, the substantially crosslinked first polymer matrix formed is with a catalyst and an additional precursor (crosslinking agent) in the presence of the refraction and/or shape modifying modulating composition. Under either scenario, the RSMC components must be compatible with and not appreciably interfere with the formation of the substantially crosslinked first polymer matrix. Similarly, the formation of a reaction product or polymer matrix from the RSMC components should also be compatible with the existing substantially crosslinked first polymer matrix. Put another way, the substantially crosslinked first polymer matrix and any matrix produced by a second polymer formed by the RSMC should not phase separate, and light transmission of the resulting optical element should be unaffected.

The RSMC as defined herein may be a single compound or a combination of compounds capable of a stimulus-induced polymerization, preferably photo-polymerization. As used herein, the term "polymerization" refers to a reaction wherein at least one of the components of the composition reacts to form at least one covalent or physical bond with either a like component or with a different component. The identities of the substantially crosslinked first polymer matrix formed according to the method and the RSMC compositions utilized in the method will depend on the end use of the optical element. But as a general rule, the components that yield the substantially crosslinked first polymer matrix and the RSMC are selected such that the components that comprise the RSMC are capable of diffusion within the substantially crosslinked first polymer matrix. Put another way, a loose first polymer matrix (lower crosslinking density), will tend to be paired with larger RSMC components and a more tightly crosslinked first polymer matrix will tend to be paired with smaller RSMC components.

Upon exposure to an appropriate energy source (e.g., heat or light or pressure or electromagnetic stimulus), the refraction and/or shape modifying modulating composition forms a reaction product (e.g., second polymer matrix) in the exposed region of an optical element prepared from materials used in the inventive method. The presence of a second polymer matrix changes the material characteristics of this region of the optical element to modulate its refraction and/or shape capabilities. In general, the formation of the second polymer matrix typically increases the refractive index of the affected portion of the optical element. After exposure, the refraction and/or shape modifying modulating composition in the unexposed region will migrate into the exposed region over time. The amount of RSMC migration into the exposed region is time dependent and may be precisely controlled. If enough time is permitted, the RSMC components will re-equilibrate and redistribute throughout the optical element (i.e., the first polymer matrix, including the exposed region). When the region is re-exposed to the energy source, the RSMC that has since migrated into the region polymerizes to further increase the formation of the second polymer matrix in the exposed region. The re-exposed regions need not be the same as the initially exposed region depending on the desired properties to be achieved. This process (exposure followed by an appropriate time interval to allow for diffusion) may be repeated until the exposed region of the optical element has reached the desired property (e.g., power, refractive index, or shape). At this point, the entire optical element is exposed to the energy source to "lock-in" the desired lens property by reacting all of the remaining RSMC components in the entire lens. In other words, because freely diffusable RSMC components are no longer available, subsequent exposure of the optical element to an energy source cannot further change its power. FIGS. 1 and 2 illustrate this process whereby the refractive index and shape (or radius of curvature) is changed by the above-described process, respectively (modulation followed by a lock in).

As described previously, the refraction and/or shape modifying modulating composition may be a single component or multiple components so long as: (i) it is compatible with the formation of the first polymer matrix; (ii) it remains capable of stimulus-induced polymerization after the formation of the first polymer matrix: and/or (iii) it is freely diffusable within the first polymer matrix. In preferred embodiments, the stimulus-induced polymerization is photo-induced polymerization.

The inventive optical elements have numerous applications in the electronics and data storage industries. Another application for the present invention is as medical lenses, particularly as intraocular lenses.

In general, there are two types of intraocular lenses ("IOLs"). The first type of an intraocular lens replaces the eye's natural lens. The most common reason for such a procedure is cataract. The second type of intraocular lens supplements the existing lens and functions as a permanent corrective lens. This type of lens (sometimes referred to as a phakic intraocular lens) is implanted in the anterior or posterior chamber to correct any refractive errors of the eye. In theory, the power for either type of intraocular lenses required for emmetropia (i.e., perfect focus on the retina from light at infinity) can be precisely calculated. However, in practice, due to errors in pre-operative power measurement, and/or variable lens positioning in the eye and wound healing, it is estimated that only about half of all patients undergoing IOL implantation will enjoy the best possible vision without the need for additional correction after surgery. Because prior art IOLs are generally incapable of post-surgical power modification, the remaining patients must resort to other types of vision correction such as external lenses (e.g., glasses or contact lenses) or corneal surgery, or in the worst case lens exchange. The need for these types of additional corrective measures is obviated with the use of the intraocular lenses of the present invention. An intraocular lens prepared using the inventive methods disclosed also has the additional requirement that the resulting lens be biocompatible.

Illustrative examples of a suitable substantially crosslinked first polymer matrix prepared according to the methods of the invention include: poly-acrylates such as poly-alkyl acrylates and poly-hydroxyalkyl acrylates; poly-methacrylates such as poly-methyl methacrylate ("PMMA"), poly-hydroxyethyl methacrylate ("PHEMA"), and poly-hydroxypropyl methacrylate ("PHPMA"); poly-vinyls such as poly-styrene and poly-N-vinylpyrolidone ("PNVP"); poly-siloxanes such as poly-dimethylsiloxane; polydimethyldiphenlysiloxane, poly-phosphazenes, and copolymers of thereof. U.S. Pat. No. 4,260,725 and patents and references cited therein (which are all incorporated herein by reference) provide more specific examples of suitable polymers that may be used to form the substantially crosslinked first polymer matrix.

In preferred embodiments, the substantially crosslinked first polymer matrix generally possesses a relatively low glass transition temperature ("$T_g$") such that a resulting IOL tends to exhibit fluid-like and/or elastomeric behavior, and is typically formed by crosslinking one or more starting materials, that may be polymeric, wherein each polymeric starting material includes at least one crosslinkable group. Illustrative examples of suitable crosslinkable groups include but are not limited to hydride, acetoxy, alkoxy, amino, anhydride, aryloxy, carboxy, enoxy, epoxy, halide, isocyano, olefinic, vinyl and oxime. In more preferred embodiments, each polymeric starting material includes terminal monomers (also referred to as endcaps) that are either the same or different from the one or more monomers that comprise the polymeric starting material but include at least one crosslinkable group. In other words, the terminal monomers begin and end the polymeric starting material and include at least one crosslinkable group as part of its structure. Although it is not necessary for the practice of the present invention, the mechanism for crosslinking the polymeric starting material to form the substantially crosslinked first polymer matrix preferably is different from the mechanism for the stimulus-induced polymerization of the components that comprise the refraction and/or shape modifying modulating composition. For example, if the RSMC is polymerized by photo-induced polymerization, then it is preferred that the polymeric starting materials have crosslinkable groups that are polymerized by any mechanism other than photo-induced polymerization.

An especially preferred class of polymeric starting materials for the formation of the substantially crosslinked first polymer matrix are poly-siloxanes (also know as "silicones") endcapped with a terminal monomer which includes a crosslinkable group selected from the group comprising acetoxy, amino, alkoxy, halide, hydroxy, vinyl, hydride and mercapto. Because silicone IOLs tend to be flexible and foldable, generally smaller incisions may be used during the IOL implantation procedure. An especially preferred example of a class of polymeric starting materials are those that utilize the hydrosilylation reaction between vinyl- and hydride-functionalized silicones in presence of a catalyst, preferably a platinum-metal containing complex, this general type of system being similar to the compositions described in the U.S. Pat. No. 5,411,553 and others.

In the present invention, the substantially crosslinked first polymer matrix is formed preferably in a mold. This is accomplished by injecting or dispensing the mixture of precursors from the first and second polymeric starting materials as well as the refraction-and/or shape-modifying composition and Platium catalyst into a shaped-mold and allowing the precursors to cure in the presence of the refraction- and/or shape-modifying composition. The curing is accomplished through catalytic polymerization of the first and second precursors (and the third precursor) and may occur at elevated pressure and controlled temperature(s).

Where the substantially crosslinked first polymer matrix is a silicone-based matrix, two types of precursors are required to practice of the invention. The first precursor comprises one or more vinyl-containing polyorganosiloxanes and the second precursor comprises one or more organosilicon compounds having silicon-bonded hydride groups which react with the vinyl groups of the first precursor.

The first precursor preferably has an average of at least two silicone-bonded vinyl radicals per molecule. The number of vinyl radicals can vary from two per molecule. For example, the first precursor can be a blend of two or more polyorganosiloxanes in which some of the molecules may have more than two vinyl radicals per molecule and some may have less than two vinyl radicals per molecule. Although it is not required that the silicon-bonded vinyl radicals be located in the alpha and/or omega (or terminal) positions of the polyorganosiloxanes, it is preferred that at least some of the vinyl radicals be located at these positions. The vinyl radicals are preferably located at the polymer ends because such polyorganosiloxanes are economical to produce and provide satisfactory products. However, because of the polymeric nature of the first precursor, its preparation may result in products that have some variation in structure, and some vinyls may not be in the terminal position even if the intent is to have them in these positions. Thus, the resulting polyorganosiloxanes may have a portion of the vinyl radicals located at branch sites.

The polyorganosiloxanes of the first precursor are preferably essentially linear polymers that may have some branching. The polyorganosiloxanes may have silicon-oxygen-silicon backbones with an average of greater than two organo groups per silicon atom. Preferably, the first precursor is made up of diorganosiloxane units with triorganosiloxane units for endgroups, but small amounts of monoorganosiloxane units and $SiO_2$ units may also be present. The organo radicals preferably have less than about 10 carbon atoms per radical and are each independently selected from monovalent hydrocarbon radicals such as methyl, ethyl, vinyl propyl, hexyl and phenyl, and monovalent substituted hydrocarbon radicals such as perfluoroalkylethyl radicals.

Examples of first precursor includes dimethylvinylsiloxy endblocked polydimethylsiloxane, methylphenylvinylsiloxy endblocked polydimethylsiloxane, dimethylvinylsiloxy endblocked polymethyl-(3,3,3-triflouropropyl) siloxane, dimethylsiloxy endblocked polydiorganosiloxane copolymers of dimethylsiloxane units, and methylphenylsiloxane units and methylphenylvinylsiloxy endblocked polydiorganosiloxane copolymers of dimethylsiloxane units and diphenylsiloxane units, and the like. The polydiorganosiloxane can have siloxane units such as dimethylsiloxane units, methylphenylsiloxane units, diphenylsiloxane units, methyl-(3,3,3-trifluoropropyl)siloxane units, monomethylsiloxane units, monophenylsiloxane units, dimethylvinylsiloxane units, trimethylsiloxane units, methylphenylvinylsiloxane units, and $SiO_2$ units. Polyorganosiloxanes of the first precursor can be single polymers or mixtures of polymers. These polymers may have at least fifty percent of the organic radicals as methyl radicals. Many polyorganosiloxanes useful as the first precursor are known in the art and are commercially available. A preferred first precursor is polydimethylsiloxane and/or polydimethyldiphenylsiloxane, or copolymers of thereof endblocked with dimethylvinylsiloxy units or methylphenylsiloxy units having a viscosity of from about 500 to 200,000 centipoise at 25° C.

The second precursor includes organosilicon compounds containing at least 2, and preferably at least 3, silicon-bonded hydride groups, i.e., hydrogen atoms, per molecule. Each of the silicon-bonded hydride groups is preferably bonded to a different silicon atom. The remaining valences of the silicon atom arc satisfied by divalent oxygen atoms or by monovalent radicals, such as alkyl having from 1 to about 6 carbon atoms per radical, for example methyl, ethyl, propyl, isopropyl, butyl, tertiary butyl, pentyl, hexyl, cyclohexyl, substituted alkyl radicals, aryl radicals, substituted aryl radicals and the like. The silicon-bonded hydride group containing organosilicon compounds can be homopolymers, copolymers and mixtures thereof which contain siloxane units of the following types: $RSiO_{1.5}$, $R_2SiO$, $R_3SiO_{0.5}$, $RHSiO$, $HSiO_{1.5}$, $R_2HSiO_{0.5}$, $H_2SiO$, $RH_2 SiO_{0.5}$, and $SiO$ where R is the monovalent radical, for example, as defined above. Examples include polymethylhydrogensiloxane cyclics, copolymers of trimethylsiloxy and methylhydrogensiloxane, copolymers of dimethylhydrogensiloxy and methylhydrogensiloxane, copolymers of trimethylsiloxy, dimethylsiloxane and methylhydrogensiloxane, copolymers of dimethylhydrogensiloxane, dimethylsiloxane and methylhydrogensiloxane and the like.

The first and second precursors are combinable in various ratios such that they produce a substantially crosslinked first polymer matrix suitable for optical elements, in particular, IOLs. That is to say, a material produced according to a method of the invention will possess physical and chemical properties that will allow the composition to function in the intended manner.

An additional composite comprising a third precursor that may function as a crosslinker may be included in the invention. This material may be the same or different from the first or second precursors and may be used to tailor the viscoelastic properties of materials produced according to certain preferred embodiments of the invention. This may be a multifunctional silicone of certain molecular weight, branched structure and functionality. It may be a vinyl-containing material, or a hydride-containing material of certain molecular weight, branched structure and functionality, for example, methylhydrocyclosiloxane, $C_5H_{20}O_5Si_5$ (CAS-68037-53-6), and other functionally similar materials. These materials may be added to the other composites depending on the specific functional groups involved and the properties desired. Preferred third precursors include but are not limited to cyclic siloxanes having silicone bonded hydride groups (as above) or silicon bonded vinyl groups wherein there are sufficient reactive groups that when they are included in materials prepared according to the invention that values for certain viscoelastic properties, which determine how IOLs will perform for example the viscous shear loss modulus, $G''$, may be controlled, to a desired value.

Rheological properties of polymers may be used to understand structure and in turn how the structure affects a polymers performance in a particular application. Rheology may be used to understand the effects of variations in formulations, molecular weight, molecular weight distribution and crosslinking density. In particular, the dynamic mechanical properties of polymers measured in a shear mode, at low degrees of strain (typically less than about 2-3 percent-strain known as the so-called "linear viscoelastic region of strain"), may be used. The measured properties include the shear complex modulus and its components the shear storage modulus ($G'$) and the shear loss modulus ($G''$). The values of which are seen to change with shear rate or frequency measured in radians/second (rads/sec). Typically, a frequency range of several orders of magnitude will be measured, for example a frequency range of 0.01 rads/sec to about 100 rads/sec. Such a range is useful in determining properties of crosslinked systems having varying degrees of crosslinking The analytical technique useful to study such properties is often referred to as Dynamic Mechanical Spectroscopy or Analyer (DMS or DMA). These properties and techniques are well known to one of ordinary skill in the polymer arts and the present disclosure is not intended to be a primer into such subject matter. With a view to the present invention, comprising a substantially crosslinked first polymer network or matrix and an RSMC, DMA may be used to compare the effect of various formulations on the rheological properties, in particular the shear loss modulus, $G''$, and determine ranges for its values that are particularly useful in preferred formulations of the present invention.

Because IOLs are required to be both flexible and foldable and yet maintain a particular shape, a technique that can predict a formulation properties can be beneficial. Thus, DMA may be utilized to understand the effects of crosslinking on varying RSMC content and/or the addition of a third precursor comprising a crosslinking agent and compare these values to thereby determine useful formulations as indicated by the appended Tables and Graphs. FIG. 1 shows the effect on the shear loss modulus of varying amounts of the RSMC of 1,000 g/mole bismethacrylate endcapped dimethylsiloxane macromer. The values for $G''$ are seen to decrease with an increase in the RSMC concentration. FIG. 2 illustrates the effect on the $G''$ by varying the content of a crosslinking agent: these values are seen to increase with increasing crosslinker content at a constant level of RSMC. Also, substantially constant or linear values over the frequency range measured of $G''$ is taken as indicative of crosslinking (or forming a crosslinked network) for the purpose of the present disclosure. Accordingly, by defining the ranges of $G''$ of various formulations prepared by embodiments of the present invention, a range of useful IOLs may be prepared. Such ranges are shown in FIGS. 1 and 2 for materials prepared using embodiments of the present invention. In particularly preferred embodiment, a fabricated optical element, comprising a reaction product of: (a) a first composite, said first composite further comprising at least one polyorganosiloxane molecule having at least two silicone-bonded vinyl radicals per molecule; and (b) a second precursor comprising at least one polyorganosiloxane molecule having at least three silicone-hydride groups per molecule; and (c) a platinum group metal-containing catalysts known to catalyze the addition of silicone-bonded hydrides to silicone-vinyl radicals; and (d) a refraction and/or shape-modifying composition; may exhibit a shear loss modulus, between $1 \times 10^4$ to about $1.25 \times 10^5$ Pa over a testing frequency range of from 0.01 radians/second to about 100 radians/second. In another preferred embodiment, a fabricated optical element further comprising a crosslinking agent selected from the group of silicone compounds and having at least three vinyl groups per molecule, silicone compounds having at least three silicone hydride moieties per molecule, the hydrides being on different silicon atoms, or combinations thereof, with the crosslinking agent being present in an amount up to about 10 weight percent of the optical element exhibits a shear loss modulus, G" of at least about $1 \times 10^4$ or higher, depending on the degree of crosslinking that is obtainable using the methods of the present invention.

A platinum group metal containing catalyst component is preferably used in embodiments of the invention. The platinum group metal catalyst component can be any of the compatible platinum group metal-containing catalysts known to catalyze the addition of silicone-bonded hydrogen atoms (hydride groups) to silicon-bonded vinyl radicals. Platinum group metal-containing catalysts can be any of the known forms which are compatible, such as platinic chloride, salts of platinum, chloroplatinic acid and various complexes, for example silicone complexes with platinum metal-containing groups. The platinum group metal-containing catalyst can be used in any catalytic quantity, such as in an amount sufficient to provide at least about 0.1 ppm weight of platinum group metal (calculated as elemental metal) based on the combined weight of the first and second precursors. Preferably, at least about 10 ppm, for example, at least about 20 ppm or at least 30 ppm or at least about 40 ppm, by weight of platinum group metal based on the combined weight of the first and second precursors is used.

The refraction- and/or shape-modifying composition (RSMC) that is used in fabricating implants of the invention is as described above and it has the preferred requirement of biocompatibility. The refraction- and/or shape-modifying composition is capable of stimulus-induced polymerization and may be a single component or multiple components so long as: (i) it is compatible with the formation of the substantially crosslinked first polymer matrix; (ii) it remains capable of stimulus-induced polymerization after the formation of the first polymer matrix; (iii) it is freely diffusable within the first polymer matrix. In general, the same type of monomers that are used to form the substantially crosslinked first polymer matrix may be used as a component of the RSMC. The monomers will often contain functional groups that are capable of stimulus-induced polymerization. However, it is preferred that the refraction- and/or shape-modifying composition is diffusable within the first polymer matrix, the refraction- and/or shape-modifying composition generally tend to be smaller (i.e., have lower molecular weights) than the first polymer matrix network, i.e., the diffusable RSMC materials have to be of molecular weight less than for instance the molecular weight between crosslinks of the substantially crosslinked first polymer matrix (this concept being well known). In addition to the one or more monomers, the refraction- and/or shape-modifying composition may include other components such as initiators and sensitizers that facilitate the formation of the second reaction product (or second polymer matrix) from the RSMC. In addition, to provide UV-blocking properties similar to those of the natural eye, UV-absorbers may also be incorporated as a component of the refraction- and/or shape-modifying composition.

In preferred embodiments, the stimulus-induced polymerization is photo-polymerization. In other words, the one or more components that comprise the refraction and/or shape modifying modulating composition each preferably includes at least one group that is capable of photopolymerization. Illustrative examples of such photopolymerizable groups include but are not limited to acrylate, allyloxy, cinnamoyl, methacrylate, stibenyl, and vinyl. In more preferred embodiments, the RSMC includes a photoinitiator (or any compound used to generate free radicals) either alone or in the presence of a sensitizer. Examples of suitable photoinitiators include acetophenones (e.g., a-substituted haloacetophenones, and diethoxyacetophenone); 2,4-dichloromethyl-1,3,5-triazines; benzoin methyl ether; and o-benzoyl oximino ketone. Examples of suitable sensitizers include p-(dialkylamino)aryl aldehyde; N-alkylindolylidene; and bis[p-(dialkylamino)benzylidene] ketone. In another embodiment, the RSMC includes a UV absorber(s). Examples of UV absorbers include but not limited to family of benzophenone and benzotriazole.

Because of the preference for flexible and foldable IOLs, an especially preferred class of RSMC is poly-siloxanes endcapped with a terminal siloxane moiety that includes a photopolymerizable group. An illustrative representation of such a RSMC macromer is

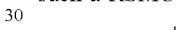

wherein Y is a siloxane which may be a monomer, a homopolymer or a copolymer formed from any number of siloxane units, and X and $X^1$ may be the same or different and are each independently a terminal siloxane moiety that includes a photopolymerizable group. An illustrative example of Y include

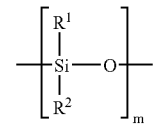

and

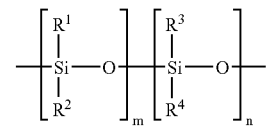

wherein: m and n are independently each an integer and $R^1$, $R^2$, $R^3$, and $R^4$ are independently each hydrogen, alkyl (primary, secondary, tertiary, cyclo), aryl, or heteroaryl. In preferred embodiments, $R^1$, $R^2$, $R^3$, and $R^4$ is a $C_1$-$C_{10}$ alkyl or phenyl. Because RSMC macromer with a relatively high aryl content have been found to produce larger changes in the refractive index of the inventive lens, it is generally preferred that at least one of $R^1$, $R^2$, $R^3$, and $R^4$ is an aryl, particularly phenyl. In more preferred embodiments, $R^1$, $R^2$, and $R^3$ are the same and are methyl, ethyl or propyl and R4 is phenyl. In another preferred embodiments, $R^1$, $R^2$, $R^3$, and $R^4$ are methyl.

Illustrative examples of X and $X^1$ (or $X^1$ and X depending on how the RSMC macromer is depicted) are

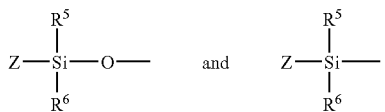

respectively wherein:

$R^5$ and $R^6$ are independently each hydrogen, alkyl, aryl, or heteroaryl; and Z is a photopolymerizable group.

In preferred embodiments, $R^5$ and $R^6$ are independently each a $C_1$-$C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, $R^5$ and $R^6$ is methyl, ethyl, or propyl and Z is a photopolymerizable group that includes an acrylate or methacrylate moiety.

In especially preferred embodiments, an RSMC macromer is of the following formula

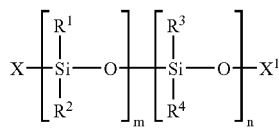

wherein X and $X^1$ are the same and $R^1$, $R^2$, $R^3$, and $R^4$ are as defined previously. Illustrative examples of such RSMC macromers include dimethylsiloxane-diphenylsiloxane copolymer endcapped with a vinyl dimethylsilane group; dimethylsiloxane-methylphenylsiloxane copolymer endcapped with a methacryloxypropyl dimethylsilane group; and dimethylsiloxane endcapped with a methacryloxypropyldimethylsilane group.

Although any suitable method may be used, a ring-opening reaction of one or more cyclic siloxanes in the presence of triflic acid has been found to be a particularly efficient method of making one class of inventive RSMC macromers. Briefly, the method comprises contacting a cyclic siloxane with a compound of the formula

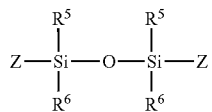

In the presence of triflic acid wherein $R^5$, $R^6$, and Z are as defined previously. The cyclic siloxane may be a cyclic siloxane monomer, homopolymer, or copolymer. Alternatively, more than one cyclic siloxane may be used. For example, a cyclic dimethylsiloxane tetramer ($D_4$) and a cyclic methyl-phenylsiloxane trimer ($D_3'$) are contacted with bis-methacryloxypropyltetramethyldisiloxane (end group) in the presence of triflic acid to form a dimethyl-siloxane methyl-phenylsiloxane copolymer that is endcapped with a methacryloxylpropyl-dhethylsilane group, an especially preferred RSMC macromer. Another preferred RSMC macromer is synthesized by contacting only with $D_4$ With the end group to form a dimethylsiloxane endcapped with a methacryloxylpropyl-dhethylsilane group.

The inventive IOLs may be fabricated with variations in the inventive method that results in a substantially crosslinked first polymer matrix with one or more components which comprise the RSMC dispersed therein, and wherein the RSMC is capable of stimulus-induced polymerization to form a second polymer matrix. In general, the method for making an inventive IOL is the same as that for making an inventive optical element: the general method of the invention having been described above. But the type of molding, (e.g. injection, compression, etc.) will depend on the optical element being made. For example, if the optical element is a prism, then a mold in the shape of a prism is used. Similarly, if the optical element is an intraocular lens, then an intraocular lens mold is used and so forth. Accordingly, the inventive method may include variations in the temperature of preparation and/or the temperature used to prepare optical elements, such as IOLs. Pressures used to prepare optical elements according to certain embodiments of the invention may vary from about atmospheric pressure (that is, a pressure within the typical variations in normal atmospheric pressure as would be understood by one of ordinary skill in the art) to an elevated pressure. In certain embodiments, the pressure may range up to and above about 20,000 pounds. In more preferred embodiments the pressures may range from about 10,000 to about 15,000 pounds.

Generally, the temperature range for preparing optical elements according to certain embodiments of the invention may vary from about the freezing point of the reaction mixture (where diffusion of reactive centers starts) used to form the substantially crosslinked first polymer matrix up to the decomposition temperature of a catalyst used in the method. In another embodiment of the invention, the temperature may range from about room temperatures to about 50 degrees centigrade. In certain preferred embodiments, the temperature may range from about 30 to about 40 degrees centigrade.

Also, in certain embodiments, the temperature(s) and/or pressure(s) may be constant or variable or may be combinations of constant and variable temperature(s) or pressures(s). Within the context of the present invention the term "about" is construed to indicate normal variations in measured values.

A key advantage of the present method as it relates to preparing an intraocular lens is that an IOL property may be modified noninvasively after implantation within the eye. For example, any errors in the power calculation due to imperfect ocular length and corneal measurements and/or variable lens positioning and wound healing may be modified noninvasively in-situ in a post surgical outpatient procedure.

In addition to the change in the IOL refractive index, the stimulus-induced formation of the second polymer matrix has been found to affect the IOL power by altering the lens curvature in a predictable manner. Additionally the ability to control the viscoelastic properties (i.e. the crosslinking density) of a lens produced according to the present method provides further control over the modulation of the ultimate IOL. As a result, both mechanisms may be exploited to modulate an IOL property, such as power, after it has been implanted within the eye. In general, the method for implementing an IOL having a substantially crosslinked first polymer matrix and a RSMC dispersed therein, comprises:

(a) exposing at least a portion of the lens to a stimulus whereby the stimulus induces the reaction of the RSMC to form a second reaction product: this may take the form of a polymerization reaction that may form an interpenetrating polymer network (IPN). If after implantation and wound healing, no IOL property needs to be modified, then the exposed portion is the entire lens. The exposure of the entire lens will lock-in the then-existing properties of the implanted lens.

However, if a lens characteristic such as its power needs to be modified, then only a portion of the lens (something less than the entire lens) would be exposed. In one embodiment, the method of implementing the inventive IOL further comprises:

(b) waiting an interval of time; and (c) re-exposing the portion of the lens to the stimulus.

This procedure generally will induce further reaction (e.g. polymerization) of the RSMC within the exposed lens portion. Steps (b) and (c) may be repeated any number of times until the intraocular lens (or optical element) has reached the desired lens characteristic. At this point, the method may further include the step of exposing the entire lens to the stimulus to lock-in the desired lens property.

In another embodiment, where a lens property needs to be modified, a method for implementing an inventive IOL comprises:

(a) exposing a first portion of the lens to a stimulus whereby the stimulus induces the polymerization of the RSMC; and exposing a second portion of the lens to the stimulus.

The first lens portion and the second lens portion represent different regions of the lens although they may overlap. Optionally, the method may include an interval of time between the exposures of the first lens portion and the second lens portion. In addition, the method may further comprise re-exposing the first lens portion and/or the second lens portion any number of times (with or without an interval of time between exposures) or may further comprise exposing additional portions of the lens (e.g., a third lens portion, a fourth lens portion, etc.). Once the desired property has been reached, then the method may further include the step of exposing the entire lens to the stimulus to lock-in the desired lens property.

In general, the location of the one or more exposed portions will vary depending on the type of refractive error being corrected. For example, in one embodiment, the exposed portion of the IOL is the optical zone which is the center region of the lens (e.g., between about 4 mm about 5 mm in diameter). Alternatively, the one or more exposed lens portions may be along IOL's outer periphery or along a particular meridian. In preferred embodiments, the stimulus is light. In more preferred embodiments, the light is from a laser source.

EXAMPLES

Example 1

Materials comprising various amounts of (a) poly-dimethylsiloxane endcapped with diacetoxymethylsilane ("PDMS") (36,000 g/mol), (b) dimethylsiloxane-diphenylsiloxane copolymer endcapped with vinyl-dimethyl silane ("DMDPS") (15,500 g/mol), and (c) a UV-photoinitiator, 2,2-dimethoxy-2-phenylacetophenone ("DMPA") as shown by Table 1 were made and tested. PDMS is the polymeric precursor which forms first polymer matris, and DMDPS and DMPA together comprise the RSMC.

TABLE 1

| PDMS (wt. %) | DMDPS (wt. %) | DMPA (wt. %)[a] |
|---|---|---|
| 90 | 10 | 1.5 |
| 80 | 20 | 1.5 |
| 75 | 25 | 1.5 |
| 70 | 30 | 1.5 |

[a]wt % with respect to DMDPS.

Briefly, appropriate amounts of PDMS (Gelest DMS-D33; 36,000 g/mol), DMDPS (Gelest PDV-0325; 3.0-3.5 mole % diphenyl, 15,500 g/mol), and DMPA (Aldrich; 1.5 wt % with respect to DMDPS) were weighed together in an aluminum pan, manually mixed at room temperature until the DMPA dissolved, and degassed under pressure (5 mtorr) for 2-4 minutes to remove air bubbles. Photosensitive prisms were fabricated by pouring the resulting silicone mixture into a mold made of three glass slides held together by scotch tape in the form of a prism and sealed at one end with silicone caulk. The prisms are ~5 cm long and the dimensions of the three sides are ~8 mm each. The PDMS in the prisms was moisture cured and stored in the dark at room temperature for a period of 7 days to ensure that the resulting first polymer matrix was non-tacky, clear, and transparent.

The amount of photoinitiator (DMPA at 1.5 weight %) was based on prior experiments with fixed RSMC macromer content of 25% in which the photoinitiator content was varied. Maximal refractive index modulation was observed for compositions containing 1.5% and 2 wt. % photoinitiator while saturation in refractive index occurred at 5 wt. %.

Example 2

Synthesis of RSMC Macromers

As illustrated by Scheme 1, commercially available cyclic dimethylsiloxane tetramer ("D$_4$"), cyclic methylphenylsiloxane trimer ("D$_3$'") in various ratios were ring-opened by triflic acid and bis-methacryloxylpropyltetramethyldisiloxane ("MPS") were reacted in a one pot synthesis. U.S. Pat. No. 4,260,725; Kunzler, J. F., Trends in Polymer Science, 4: 52-59 (1996); Kunzler et al., J. Appl. Poly. Sci., 55: 611-619 (1995); and Lai et al., J. Poly. Sci. A. Poly. Chem., 33: 1773-1782 (1995).

SCHEME 1

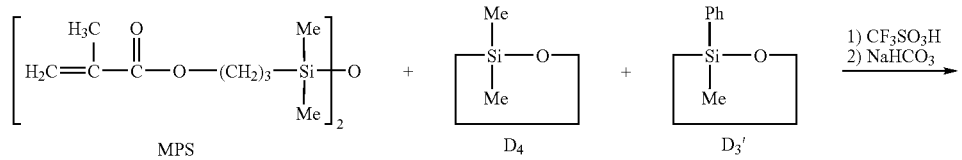

-continued

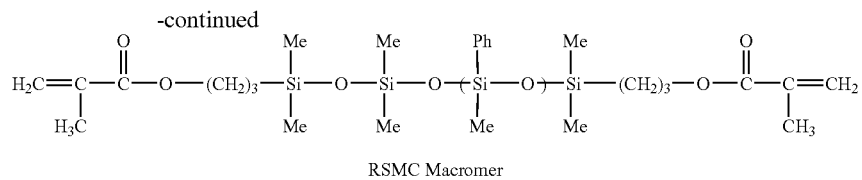
RSMC Macromer

Briefly, appropriate amounts of MPS, $D_4$, and $D_3'$ were stirred in a vial for 1.5-2 hours. An appropriate amount of triflic acid was added and the resulting mixture was stirred for another 20 hours at room temperature. The reaction mixture was diluted with hexane, neutralized (the acid) by the addition of sodium bicarbonate, and dried by the addition of anhydrous sodium sulfate. After filtration and rotoevaporation of hexane, the RSMC macromer was purified by further filtration through an activated carbon column. The RSMC macromer was dried at 5 mtorr of pressure between 70-80° C. for 12-18 hours.

The amounts of phenyl, methyl, and endgroup incorporation were calculated from $^1$H-NMR spectra that were run in deuterated chloroform without internal standard tetramethylsilane ("TMS"). Illustrative examples of chemical shifts for some of the synthesized RSMC macromers follows. A 1,000 g/mole RSMC macromer containing 5.58 mole % phenyl (made by reacting: 4.85 g (12.5 mmole) of MPS; 1.68 g (4.1 mole) of $D_3'$; 5.98 g (20.2 mmole) of $D_4$; and 108 μl(1.21 mmole) of triflic acid: δ=7.56-7.57 ppm (m, 2H) aromatic, δ=7.32-7.33 ppm (m, 3H) aromatic, δ=6.09 ppm (d, 2H) olefinic, δ=5.53 ppm (d, 2H) olefinic, δ=4.07-4.10 ppm (t, 4H) —O—C$\underline{H}_2$CH$_2$CH$_2$—, δ=1.93 ppm (s, 6H) methyl of methacrylate, δ=1.65-1.71 ppm (m, 4H) —O—CH$_2$C$\underline{H}_2$CH$_2$—, δ=0.54-0.58 ppm (m, 4H) —O—CH$_2$CH$_2$C$\underline{H}_2$—Si, δ=0.29-0.30 ppm (d, 3H), C$\underline{H}_3$—Si-Phenyl, δ=0.04-0.08 ppm (s, 50 H) (CH$_3$)$_2$Si of the backbone.

A 2,000 g/mole RSMC macromer containing 5.26 mole % phenyl (made by reacting: 2.32 g (6.0 mmole) of MPS; 1.94 g (4.7 mmole) of $D_3'$; 7.74 g (26.1 mmole) of $D_4$; and 136 μl (1.54 mmole) of triflic acid: δ=7.54-7.58 ppm (m, 4H) aromatic, 6=7.32-7.34 ppm (m, 6H) aromatic, δ=6.09 ppm (d, 2H) olefinic, δ=5.53 ppm (d, 2H) olefinic, δ=4.08-4.11 ppm (t, 4H) —O—C$\underline{H}_2$CH$_2$CH$_2$—, δ=1.94 ppm (s, 6H) methyl of methacrylate, δ=1.67-1.71 ppm (m, 4H) —O—CH$_2$C$\underline{H}_2$CH$_2$13 , δ=0.54-0.59 ppm (m, 4H) —O—CH$_2$CH$_2$C$\underline{H}_2$—Si, 6=0.29-0.31 ppm (m, 6H), C$\underline{H}_3$—Si-Phenyl, δ=0.04-0.09 ppm (s, 112H) (CH$_3$)$_2$Si, of the backbone.

A 4,000 g/mole RSMC macromer containing 4.16 mole % phenyl (made by reacting: 1.06 g (2.74 mmole) of MPS; 1.67 g (4.1 mmole) of $D_3'$; 9.28 g (31.3 mmole) of $D_4$; and 157 μl. (1.77 mmole) of triflic acid: μ=7.57-7.60 ppm (m, 8H) aromatic, δ=7.32-7.34 ppm (m, 12H) aromatic, δ=6.10 ppm (d, 2H) olefinic, δ=5.54 ppm (d, 2H) olefinic, δ=4.08-4.12 ppm (t, 4H) —O—C$\underline{H}_2$CH$_2$CH$_2$—, δ=1.94 ppm (s, 6H) methyl of methacrylate, δ=1.65-1.74 ppm (m, 4H) —O—CH$_2$C$\underline{H}_2$CH$_2$—, δ=0.55-0.59 ppm (m, 4H) —O—CH$_2$CH$_2$C$\underline{H}_2$—Si; δ=0.31 ppm (m, 11H), C$\underline{H}_3$—Si-Phenyl, δ=0.07-0.08 ppm (s, 272H) (CH$_3$)$_2$Si of the backbone.

Similarly, to synthesize dimethylsiloxane polymer without any methylphenylsiloxane units and endcapped with methyacryloxypropyl dimethylsilane, the ratio of $D_4$ to MPS was varied without incorporating $D_3'$.

Molecular weights were calculated by $^1$H-NMR and by gel permeation chromatography ("GPC"). Molecular weights were obtained by universal calibration method using polystyrene and poly(methyl methacrylate) standards. Table 2 shows the characterization of other RSMC macromers synthesized by the triflic acid ring opening polymerization.

TABLE 2

| Mole % Phenyl | Mole % Methyl | Mole % Methacrylate | Mn (NMR) | Mn (GPC) | $n_D$ |
|---|---|---|---|---|---|
| 6.17 | 87.5 | 6.32 | 1001 | 946 | 1.44061 |
| 3.04 | 90.8 | 6.16 | 985 | 716 | 1.43188 |
| 5.26 | 92.1 | 2.62 | 1906 | 1880 | — |
| 4.16 | 94.8 | 1.06 | 4054 | 4200 | 1.42427 |
| 0 | 94.17 | 5.83 | 987 | 1020 | 1.42272 |
| 0 | 98.88 | 1.12 | 3661 | 4300 | 1.40843 |

Where Mn = number average molecular weight, and $n_D$ = refractive index measured at sodium D-line At 10-40 wt %, these RSMC macromers of molecular weights 1000 to 4000 g/mol with 3-6.2 mole % phenyl content are completely miscible, biocompatible, and form optically clear prisms and lenses when incorporated in the silicone matrix. RSMC macromers with high phenyl content (4-6 mole %) and low molecular weight (1,000-4,000 g/mol) resulted in increases in refractive index change of 2.5 times and increases in speeds of diffusion of 3.5 to 5.0 times compared to the RSMC macromer used in Table 1 (dimethylsiloxane-diphenylsiloxane copolymer endcapped with vinyldimethyl silane ("DMDPS") (3-3.5 mole % diphenyl content, 15,500 g/mol).

Example 3

By mixing 0.23% of photoinitiator (Irgacure 651, Ciba) in 30% 1,000 g/mole bismethacrylate endcapped polydimethylsiloxane (RSMC macromer), the refraction and/or shape modifying modulating composition was made. To this mixture, 70% of 36,000 g/mole diacetoxymethylsilyl endcapped polydimethylsiloxane (first precuror) was added and the entire composition mixed well. The mixture was degassed under vacuum for 10 minutes and then transferred to a syringe. Using 20-gauge cannula, the final formulation was injected in a bubble of a bubble wrap plastic (i.e. "mold") and allowed to cure at room temperature for a period of 24 hours. The cured material conformed to the shape of the bubble and possessed desired mechanical properties.

Example 4

By mixing 0.23% of photoinitiator (Irgacure 651, Ciba), and 0.02% of UVAM UV-absorber (2(2'-hydroxy-3'-t-butyl-5'-vinylphenyl)-5-chloro-2H-benzotriazole, Chemica) in 30% 1,000 g/mole bismethacrylate endcapped dimethylsiloxane methylphenylsiloxane copolymer (macromer), the RSMC was made. To this mixture, 35% of Part B liquid component of a commercial silicone (MED-6820, NuSil)

and 1-5% of methylhydrocyclosiloxane crosslinker was added and the entire composition mixed and degassed under vacuum for 10 minutes. Finally to this mixture, 35% of Part A liquid component of a commercial silicone (MED-6820, NuSil) and a drop of Platinum catalyst (PC075, United Chemical Technology) were added and the composition mixed and degassed under vacuum. The final formulation was transferred to a syringe. Using 20 Gauge cannula, it was injected in a bubble of a bubble wrap plastic or in an oral dosage capsule that was drained of its pharmaceutical contents Vitamin E. The silicone mixture was allowed to cure for a period of 24 hours at 40° C. The cured material conformed to the shape of the bubble or capsule and possessed desired mechanical properties.

Example 5

By mixing 0.23% of photoinitiator (Irgacure 651, Ciba), 0.02% of UV-absorber (UVAM) in 30% 1,000 g/mole bismethacrylate endcapped polydimethylsiloxane (macromer), the RSMC was made. To this mixture, 35% of Part B liquid component of a commercial silicone (MED-6033, NuSil) and about 1-5% of methylhydrocyclosiloxane (CAS-68037-53-6) crosslinker was added and the entire composition mixed and degassed under vacuum for 10 minutes. Finally to this mixture, 35% of Part A liquid component of a commercial silicone (MED-6033, NuSil) and a drop of Platinum catalyst (PC075, United Chemical Technology) were added and the composition mixed and degassed under vacuum. The final formulation was transferred to a syringe. Using 20 gauge cannula, it was injected in a bubble of a bubble wrap plastic serving as a mold. The silicone mixture was allowed to cure for a period of 24 hours at 350° C. The cured material conformed to the shape of the bubble and possessed desired mechanical properties.

Example 6

By mixing 0.23% of photoinitiator (Irgacure 651, Ciba), 0.02% of UV-absorber (UVAM) in 30% of 1,000 g/mole bismethacrylate endcapped polydimethylsiloxane (macromer), the RSMC was made. To this mixture, 35% of silicone base polymer (similar to that used in MED-6820) and appropriate amount of crosslinker were added and the entire composition mixed and degassed under vacuum for 10 minutes. Finally, to this mixture, 35% of base polymer along with the platinum catalyst were added and the composition mixed and degassed under vacuum. The final formulation was transferred to a syringe. Using 20 gauge cannula, it was injected in a bubble of a bubble wrap plastic or in a sac made by gluing the edges of two contact lenses to form a mold. The resulting silicone mixture was allowed to cure for a period of 24 hours at 35° C. The cured material conformed to the shape of the mold used and possessed desired mechanical properties.

Example 7

In a vial, 0.00152 g of Irgacure 369 (Ciba, 2-Benzyl-2-dimethylamino-1-(4-morpholinophenyl)-butanone-1) photoinitiator was mixed with 0.00160 g of UVAM UV-absorber and 1.20000 g of 1,000 g/mole of macromer were weighed and mixed thoroughly. To this vial, 1.40000 g of Part B of a commercial silicone MED silicone 6820 (a two part silicone elastomer made by NuSil Technology, lot no. 20982) was added and the contents mixed thoroughly and labeled. Next, in another vial, 1.40000 g of Part A of a commercial silicone MED 6820 (NuSil Technology, lot no. 20982) was weighed with 0.01540 g of a platinum-containing catalyst PC075 (Pt-divinyltetramethyldisiloxane complex, UCT, lot no. 2005060) ( ), the contents mixed thoroughly and labeled. Both vials were degassed under vacuum to remove air bubbles. To the vial containing the first mixture 1.4 g of the second mixture was added and the contents mixed thoroughly. The entire mixture (~4 g) was degassed and poured on a chrome plate (2×2 in) having a 1 mm thick spacer and another chrome plate was placed on top to form a compression mold. The sandwiched material was pressed at ~10,000 pounds in a Carver press maintained at 40° C. for 48 hours. A 2"×2"×1 mm cured silicone slab or film containing RSMC was recovered.

Example 8

In a vial, 0.0092 g of Irgacure 651 (Ciba, 2,2-dimethoxy-2-phenylacetophenone) photoinitiator; 0.0016 g of UVAM UV-absorber, and 1.2000 g of 1,000 g/mole of bismethacrylate endcapped polydimethylsiloxane macromer were mixed thoroughly. To this vial, 1.4000 g of Part B of a commercial silicone MED 6820 (lot no. 20982)was added and the contents mixed thoroughly and labeled. In another vial, 1.4000 g of Part A of a commercial silicone MED 6820 (lot no. 20982)was weighed and 0.0154 g of Pt-divinyltetramethyldisiloxane complex Catalyst PC075 (UCT, lot no. 2005060) was added and the contents mixed thoroughly and labeled. Both vials were degassed under vacuum to remove air. To the vial containing the first mixture, 1.4 g of the second mixture was added and the contents were mixed thoroughly. The entire mixture (~4 g) was degassed and poured on a chromed plate (2×2 in) having a 1 mm thick spacer. A second chromed plate was placed on top of the spacer and the mixture between the sandwiched chrome plates was pressed at 10000 pounds in a Carver press that was maintained at 40° C. for 48 hours to cure the material. A 2"×2"×1 mm cured silicone slab or film containing RSMC was recovered.

Example 9

In a vial, 0.0092 g of Irgacure 651 (Ciba, 2,2-dimethoxy-2-phenylacetophenone) photoinitiator, 0.0008 g of UVAM UV-absorber, and 1.2000 g of of 1,000 g/mole of bismethacrylate endcapped polydimethylsiloxane macromer were weighed and mixed thoroughly until they dissolved completely. Care was taken to protect these samples from ambient light exposure by covering the container with aluminum foil. To this vial, 1.4000 g of Part B of a commercial silicone MED 6820 (lot no. 20982) was added and the contents mixed thoroughly and labeled. In another vial, 1.4000 g of Part A of a commercial silicone MED 6820 (lot no. 20982) was weighedand 0.0184 g of the Pt-divinyltetramethyldisiloxane complex Catalyst PC075 (UCT, lot no. 2005060)was added and the contents were mixed together thoroughly and labeled. Both containers were degassed under vacuum to remove air bubbles. To the vial containing the first mixture, 1.4 g of the second mixture was added and the contents were mixed together thoroughly. The entire mixture was degassed and poured on a chromed plate (2×2 in) having a 1 mm thick spacer, and another chrome plate was placed on top, to form a compression mold. The silicone mixture between the sandwiched chrome plates was pressed at 10,000-15,000 pounds in a Carver press maintained at 40° C. for 48 hours. A 2"×2"×1 mm cured silicone slab or film containing RSMC was recovered.

Example 10

8 mm discs of 2 mm thick cut from the slabs or films prepared according to the above examples were tested using Dynamic Mechanical Spectroscopy (DMA) in shear mode over a frequency range of 0.01 to 100 rad/sec at 35° C. between parallel plates to determine the shear loss modulus, G", indicating crosslinking in elastomeric materials: a relatively constant value of G" over the frequency range tested is a positive indicator of sufficient substantial crosslinking in the IOL formulations. These Spectra are shown in FIGS. 1 and 2 and the summary of the data shown in Table 3 and 4.

TABLE 3

G" VALUES FOR RSMC MACROMER ADDITION LEVEL 0–30%
@ 0.01 and 100 Rads/Sec

| RSMC Macromer Addition Level | Rad/Sec | G" (PA) |
| --- | --- | --- |
| 0% | 0.01 | $1.61 \times 10^5$ |
| 0% | 100 | $2.19 \times 10^5$ |
| 1% | 0.01 | $9.08 \times 10^4$ |
| 1% | 100 | $1.30 \times 10^5$ |
| 2% | 0.01 | $1.03 \times 10^5$ |
| 2% | 10.0 | $1.33 \times 10^5$ |
| 5% | 0.01 | $4.08 \times 10^4$ |
| 5% | 100 | $5.51 \times 10^4$ |
| 10% | 0.01 | $3.20 \times 10^4$ |
| 10% | 100 | $4.73 \times 10^4$ |
| 20% | 0.01 | $2.59 \times 10^4$ |
| 20% | 100 | $3.56 \times 10^4$ |
| 30% | 0.01 | $2.28 \times 10^4$ |
| 30% | 100 | $3.39 \times 10^4$ |

TABLE 4

EFFECT OF METHYL CYCLOSILOXANE CROSS-LINKING AGENT ADDITION LEVELS ON G" VALUES IN A 30% RSMC-CONTAINING-SUBSTANTIALLY CROSSLINKED POLYSILOXANE MATRIX

| Sioxane Formulation Addition Level | Rad/Sec | G" (PA) |
| --- | --- | --- |
| 0% | 0.01 | $2.23 \times 10^4$ |
| 0% | 100 | $3.39 \times 10^4$ |
| 3% | 0.01 | $5.05 \times 10^4$ |
| 3% | 100 | $6.34 \times 10^4$ |
| 5% | 0.01 | $6.09 \times 10^4$ |
| 5% | 100 | $7.62 \times 10^4$ |
| 10% | 0.01 | $9.86 \times 10^4$ |
| 10% | 100 | $1.06 \times 10^5$ |

It can be seen from both the tables and graphs that as the RSMC macromer content is increased the shear loss modulus decreases indicating a decrease in the effective crosslinking of the sample. But the addition of the crosslinking agent, methyl cyclosiloxane may be used to effectively control the crosslinking in the lens material. In particular, it is noted that the addition of this particular crosslinking agent at a 10 weight % level to an optical element formulation containing 30% of a RSMC compound (Table 4) exhibits substantially similar G" values as on the formulation listed in Table 3 having only about 1% RSMC macromer addition.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The claimed invention is:

1. A method for fabricating an optical element comprising;
    (a) preparing a first composite comprising a first precursor and a refraction- and/or shape- modifying composition (RSMC);
    (b) preparing a second composite comprising a second precursor and a catalyst for the first and second precursors;
    (c) combining the first and the second composites to form a reaction mixture;
    (d) placing the reaction mixture into a mold;
    (e) forming a substantially cross-linked first polymer matrix from said reaction mixture, said substantially crosslinked first polymer matrix having said RSMC dispersed therein, and;
    (f) removing the optical element from the mold.

2. The process according to claim 1 further comprising the step of adding at least one third composite, the third composite comprising a third precursor further comprising a crosslinking agent.

3. The process according to claim 2 further comprising the step of forming the substantially crossed linked first polymer matrix under pressures.

4. The process according to claim 3 wherein the pressure is from about atmospheric pressure up to about 20,000 pounds per square inch.

5. The process according to claim 4 wherein the pressure is in the range of about 10,000 to about 20,000 pounds per square inch.

6. The process according to claim 3 wherein the pressure is constant, variable or a combination of constant and variable pressures.

7. The method of claim 2 wherein the cross-linking agent is selected from the group consisting of vinyl silicone compounds having at least three vinyl groups per molecule and silicone compounds having at least three silicone hydride moieties per molecule.

8. The method of claim 7 wherein the crosslinking agent is present is an amount of up to 15% by weight.

9. The process according to claim 1 further comprising the step of forming the reaction mixture in the mold at a temperature from above the freezing temperature of the reaction mixture to the decomposition temperature of the catalyst.

10. The process according to claim 9 wherein the temperature is in the range of about 30° C. to about 40° C.

11. The process according to claim 1 further comprising the step of forming the reaction mixture in the mold at a temperature in the range of from about room temperature to about 50° C.

12. The process according to claim 1 further comprising the step of forming the reaction mixture in the mold at a constant temperature, over a variable temperature range or a combination of constant temperature and variable temperature ranges.

13. The method of claim 1 wherein the first precursor comprises at least one polyorganosiloxane molecule having at least two silicone-bonded vinyl radials per molecule.

14. The method of claim 1 wherein the second precursor comprises at least one polyorganosiloxane molecule having at least three silicone-bonded hydride groups with the proviso that no single silicone atom has more than two Si-H bonded groups.

15. The method of claim 1 wherein the catalyst is a platinum group metal-containing catalyst known to catalyze the addition of silicone bonded hydrides to silicone-bonded vinyl radicals.

16. The method according to claim 15 wherein the catalyst is present in the reaction mixture sufficient to provide at least about 0.1 parts per million by weight of platinum group metal, calculated as elemental metal.

17. The method of claim 1 wherein the RSMC is biocompatible.

18. The method of claim 1 wherein the RSMC comprises polysiloxanes.

19. The method of claim 18 wherein the polysiloxane contains a functional group capable of stimulus-induced polymerization.

20. The method of claim 19 wherein the functional group is selected from the group comprising acrylate, alkoxy, cinnanmoyl, methacrylate, stibenyl, and vinyl.

21. The method of claim 1 wherein the refraction and/or shape modifying composition further comprises a photoinitiator.

22. The method of claim 21 wherein the photoinitiator is selected from the group comprising: acetophenone, 2,4-dichloromethyl-1,3,5 triazines, benzoin methyl ethers, O-benzoyloximino-ketone and silicone derivatives thereof.

23. The method of claim 1 further comprising the step of energetically stimulating the optical element thereby causing the RSMC to form a reaction product.

24. The method of claim 23 wherein said reaction product is polymeric or an interpenetrating polymer network.

25. The method of claim 1 wherein the RSMC comprises a macromer of the formula x-Y-x

and a photoinitiator wherein Y is

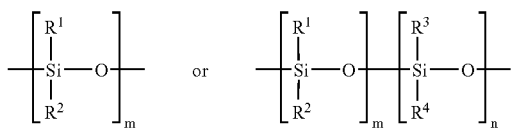

X is

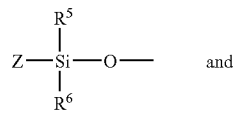 and $X^1$ is

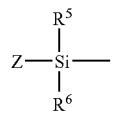

wherein: m and n are each independently an integer and $R^1$, $R^2$, $R^3$, $R^4$, $R^5$, and $R^6$ are each independently selected from the group consisting hydrogen, alkyl, aryl, and heteroaryl; and Z is a photopolymerizable The method of claim 25 wherein said $R^1$, $R^2$, and $R^3$, $R^5$, and $R^6$ are selected from the group consisting of methyl, ethyl, and propyl, and $R^4$ is pThe method of claim 1 wherein the RSMC comprises up to about 45% by weight of the optical element.

26. An optical element prepared according to any one of claims 1-25.

27. An intraocular lens prepared according to anyone of claims 1-25.

28. A fabricated optical element, comprising a reaction product of:
  (a) a first composite, said first composite further comprising at least one polyorganosiloxane molecule having at least two silicone-bonded vinyl radicals per molecule;
  (b) a second precursor comprising at least one polyorganosiloxane molecule having at least three silicone-hydride groups per molecule;
  (c) a platinum group metal-containing catalysts known to catalyze the addition of silicone-bonded hydrides to silicone-vinyl radicals;
  (d) a refraction and/or shape-modifying composition; said reaction product exhibiting a shear loss modulus, between $1 \times 10^4$ to about $1.25 \times 10^5$ Pa over a testing frequency range of from 0.01 radians/second to about 100 radians/second.
  (e) a UV-absorber(s).

29. The fabricated optical element of claim 28 further comprising a cross-linking agent selected from the group of silicone compounds having at least three vinyl groups per molecule, silicone compounds having at least three silicone hydride moieties per molecule, said hydrides being on different silicon atoms, or combinations thereof, said crosslinking-agent being present in an amount up to about 15 weight percent of the optical element.

30. The fabricated optical element of claim 28 wherein the fabricated optical element exhibits a shear loss modulus, G" of at least about $1 \times 10^4$.

* * * * *